US009622711B2

United States Patent
Zhao et al.

(10) Patent No.: US 9,622,711 B2
(45) Date of Patent: Apr. 18, 2017

(54) SYSTEM AND METHOD FOR MEASUREMENT OF SHEAR WAVE SPEED FROM MULTI-DIRECTIONAL WAVE FIELDS

(71) Applicant: MAYO Foundation for Medical Education and Research, Rochester, MN (US)

(72) Inventors: Heng Zhao, Rochester, MN (US); Pengfei Song, Rochester, MN (US); Matthew W. Urban, Rochester, MN (US); Randall Kinnick, Rochester, MN (US); Armando Manduca, Rochester, MN (US); James F. Greenleaf, Rochester, MN (US); Shigao Chen, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 14/398,854

(22) PCT Filed: Apr. 25, 2014

(86) PCT No.: PCT/US2014/035437
§ 371 (c)(1),
(2) Date: Nov. 4, 2014

(87) PCT Pub. No.: WO2015/009339
PCT Pub. Date: Jan. 22, 2015

(65) Prior Publication Data
US 2016/0262706 A1     Sep. 15, 2016

Related U.S. Application Data

(60) Provisional application No. 61/856,452, filed on Jul. 19, 2013.

(51) Int. Cl.
*A61B 5/00* (2006.01)
*A61B 8/08* (2006.01)
(Continued)

(52) U.S. Cl.
CPC ............ *A61B 5/7282* (2013.01); *A61B 5/055* (2013.01); *A61B 5/4244* (2013.01);
(Continued)

(58) Field of Classification Search
CPC ..... A61B 5/7282; A61B 5/055; A61B 5/4244; A61B 5/7257; A61B 8/485; G01N 29/043; G01N 2291/028
See application file for complete search history.

(56) References Cited

U.S. PATENT DOCUMENTS

| 6,554,770 B1 | 4/2003 | Sumanaweera et al. |
| 2010/0222678 A1 | 9/2010 | Bercoff et al. |

(Continued)

OTHER PUBLICATIONS

International Search Report under date of mailing of Sep. 9, 2014 in connection with PCT/US2014/035437.

*Primary Examiner* — Michael Rozanski
(74) *Attorney, Agent, or Firm* — Quarles & Brady LLP

(57) ABSTRACT

A system and method for measuring material properties of a medium includes producing a multi-directional wave field in the medium and detecting, with a detection system capable of detecting wave fields propagating in a medium, the multi-directional wave field in at least two spatial dimensions over at least one time instance. The system and method also include determining a lowest wave speed, calculating at least one of wave speed and material properties of the medium, and generating a report indicating the at least one of wave speed and material properties of the medium.

29 Claims, 11 Drawing Sheets

(51) Int. Cl.
*G01N 29/04* (2006.01)
*A61B 5/055* (2006.01)
*G01S 7/52* (2006.01)
*G01S 15/89* (2006.01)

(52) U.S. Cl.
CPC ............ *A61B 5/7257* (2013.01); *A61B 8/485* (2013.01); *G01N 29/043* (2013.01); *G01S 7/52022* (2013.01); *G01S 7/52042* (2013.01); *G01N 2291/028* (2013.01); *G01S 15/899* (2013.01)

(56) References Cited

U.S. PATENT DOCUMENTS

| | | |
|---|---|---|
| 2011/0263978 A1 | 10/2011 | Chen et al. |
| 2011/0319756 A1 | 12/2011 | Zheng et al. |

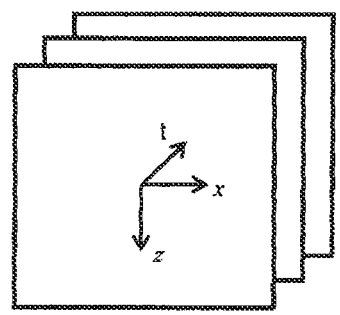 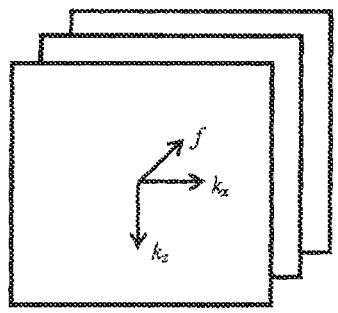
FIG. 3A  FIG. 3B
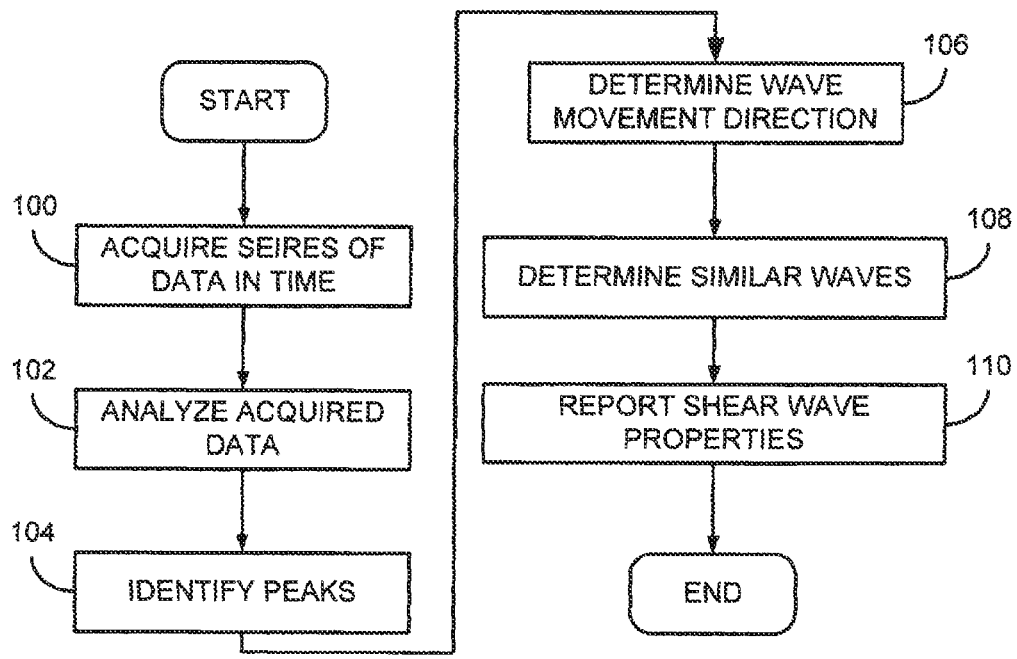
FIG. 4
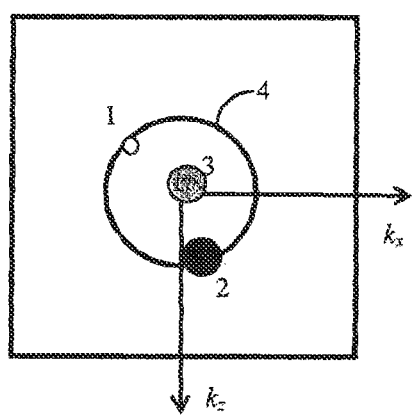
FIG. 5

SYSTEM AND METHOD FOR MEASUREMENT OF SHEAR WAVE SPEED FROM MULTI-DIRECTIONAL WAVE FIELDS

CROSS-REFERENCE TO RELATED APPLICATIONS

This application represents the national stage entry of PCT International Application No. PCT/US2014/035437 filed Apr. 25, 2014, which claims priority to, U.S. Provisional Patent Application Ser. No. 61/856,452 filed Jul. 19, 2013, both of which are incorporated herein by reference for all purposes.

STATEMENT REGARDING FEDERALLY SPONSORED RESEARCH

This invention was made with government support under DK092255, EB002167, and DK082408 awarded by the National Institutes of Health. The government has certain rights in the invention.

BACKGROUND OF THE INVENTION

The present disclosure relates to systems and methods for non-invasive analysis of properties of a medium. More particularly, the disclosure relates to systems and methods for measuring shear wave speed in a medium.

Non-invasive or non-destructive measurement of the mechanical properties of a medium is useful in a wide range of application. In particular, measuring the mechanical properties of tissues has important medical applications because it is related to tissue health state. For example, liver fibrosis is associated with increase of stiffness (shear modulus or shear elasticity) of liver tissue and thus measurement of liver stiffness can be used to non-invasively stage liver fibrosis. One way to non-invasively and non-destructively assess stiffness is using shear waves. As such, there has been increasing interest in creating and accurately measuring shear wave propagating in a medium.

Regardless of the particular system and resulting functionality being used or the underlying clinical information being sought, the use of shear waves in medical applications is increasing. As such, there is a need to provide more robust and efficient systems and methods for measuring or determining shear wave speed such in a manner appropriate for medical applications.

SUMMARY

In accordance with one aspect of the present disclosure, a method of measuring material properties of a medium is provided that includes producing a multi-directional wave field in the medium. The method also includes detecting, with a detection system capable of detecting wave fields propagating in a medium, the multi-directional wave field in at least two spatial dimensions over a period of time. The method further includes determining a lowest wave speed from the detecting and calculating at least one of wave speed and material properties of the medium based on the determining. The method includes generating a report indicating the at least one of wave speed and material properties of the medium.

In accordance with another aspect of the present disclosure, a method of producing images of properties of an object is provided that includes producing a multi-directional wave field in the object. The method also includes using an imaging device, acquiring data about the multi-directional wave field in at least two spatial dimensions over a period of time and separating the data acquired into component data propagating in different directions. The method further includes calculating at least two wave components pointing at different spatial directions from the component data and producing a wave speed map for each propagation direction using the wave components. The method includes combining wave speed maps to produce at least one of a speed image and material property image for the object.

In accordance with yet another aspect of the present disclosure, a system is provided for measuring material properties of a medium. The system includes an excitation system configured to produce a multi-directional wave field in the medium and a detection system configured to acquire data about the multi-directional wave field in at least two spatial dimensions over a period of time. The system also includes a processor configured to receive the data from the detection system, determine a lowest wave speed from the data, and calculate at least one of wave speed and material properties of the medium based on the lowest wave speed. The processor is also configured to generate a report indicating the at least one of wave speed and material properties of the medium.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIGS. 3A and 3B are a schematic diagrams illustrating spatiotemporal and k-f frequency domains, including the spatiotemporal domain for u(x,z,t) (3A) and k-f frequency domain for $U(k_x,k_z,f)$ (3B).

FIG. 4 is a flow chart of a method when analyzing a homogeneous medium.

FIG. 5 is a schematic diagram in the k-f domain showing multiple waves.

DETAILED DESCRIPTION OF THE INVENTION

Measuring the mechanical properties of tissues has important medical applications because it is related to tissue health state. For example, liver fibrosis is associated with increase of stiffness (shear modulus or shear elasticity) of liver tissue and thus measurement of liver stiffness can be used to non-invasively stage liver fibrosis. Propagation of shear waves is determined by a medium's mechanical properties. According to the Voigt model, shear wave speed $c_s$ in a medium relates to its shear modulus $\mu_1$ and viscosity $\mu_2$ by:

$$c_s(\omega_s) = \sqrt{2(\mu_1^2 + \omega_s^2 \mu_2^2) / \rho\left(\mu_1 + \sqrt{\mu_1^2 + \omega_s^2 \mu_2^2}\right)} ; \quad (1)$$

where $\omega_s$ is the frequency of the shear wave and $\rho$ is tissue density that can be assumed to be 1000 kg/m³. Neglecting viscosity (set $\mu_2=0$), Eq. (1) simplifies to:

$$c_s = \sqrt{\frac{\mu_1}{\rho}} . \quad (2);$$

where $c_s$ in Eq. (2) is the group velocity of the shear wave, meaning the averaged shear wave speed over all frequency components of the shear wave. Therefore, shear waves can be used to evaluate tissue elasticity by assuming zero viscosity and using Eq. (2) to solve for $\mu_1$, or evaluate both elasticity and viscosity by producing a shear wave in the tissue, measuring its propagation velocity at multiple frequencies, and using Eq. (1) to solve for $\mu_1$ and $\mu_2$.

Elasticity Measurements with Shear Waves

Figure 1:
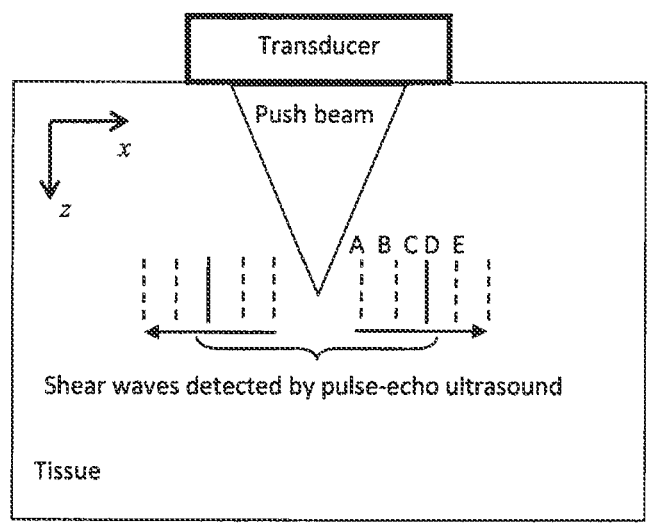
FIG. 1 is a schematic diagram illustrating a shear wave produced by an ultrasound push beam.

Ultrasound can be used to generate shear waves remotely within the tissue for noninvasive elasticity imaging. Typically, a push ultrasound beam (focused or not focused) with long duration is used to produce a transient shear wave and pulse echo ultrasound is used to detect the propagation of the shear wave, as shown in FIG. 1. Tissue particles move up and down due to the shear wave and this perturbation propagates outwards (see arrows in FIG. 1) from the push beam at propagation speed $c_s$. That is, in FIG. 1, A, B, C, D, E are positions of shear wave detection by pulse-echo ultrasound. The vertical lines represent shear wave fronts, which are moving outwards from the push center. At the example shown here, the shear wave front (represented by the solid vertical line) is at position C. The dashed lines represent the shear wave fronts that have already passed (positions A and B) or to be arriving (positions D and E).

The time profile of shear wave motion at multiple positions detected by pulse-echo ultrasound along the shear wave propagation path can be used to calculate $c_s$. For example, assuming the distance between position A and E is $\Delta r$ and the delay between the arrival time of the shear wave at these two positions is $\Delta t$, then $c_s=\Delta r/\Delta t$. The time delay $\Delta t$ can be estimated by tracking the time instance of the shear wave peak at each position, or by finding the delay that gives the maximum cross correlation between the 2 shear wave time signals detected at each position. For the example shown in FIG. 1, the shear wave fronts A-E are relatively uniform along depth direction z. Therefore, we only need to detect the shear wave along the x-direction to measure the shear wave propagation speed. In other words, a set of one-dimensional (1D) spatial data is required to correctly measure shear wave speed if the propagation direction and the detection direction are aligned.

Shear waves produced by ultrasound push beams are typically weak (micrometers), making shear wave detection, and therefore $c_s$ measurement, susceptible to noise (cardiac motion, breathing motion, body motion, ultrasound system noise, and the like). Therefore, shear wave measurements using ultrasound push beams have limited penetration. This can be problematic for applications requiring deeper penetration: for example, making shear wave measurements in livers of obese patients. Shear waves produced by mechanical vibration sources (external vibrator or internal cardiac motion) can be of much higher amplitude for more reliable measurements in deeper regions. For some applications, a multi-directional wave propagation field is desirable. To create a multi-directional vibration field one could use multiple small external vibrators that are activated in a continuous or transient manner. Additionally, a single large external vibrator could be used and driven with a continuous or transient excitation signal. Physiological motion such as that arising from the heart contraction, pressure waves in the vessels, or breathing can also be used as a source of wave motion. Each method has different advantages with respect to directionality of the waves, frequency characteristics, and motion amplitude. Shear waves thus produced typically come in multiple directions whose orientations are unknown. This can cause bias in shear wave speed measurements.

Figure 2:
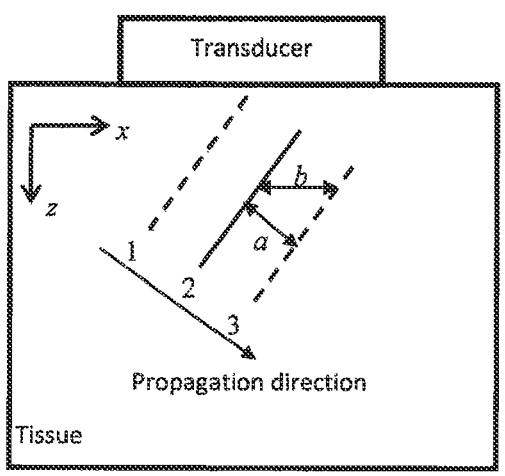
FIG. 2 is a schematic diagram illustrating that a shear wave propagating at an unknown direction can cause bias to $c_s$ measurements.

In the example shown in FIG. 2, the shear wave is propagating at an oblique angle from wave front 1 to 2 to 3. Assuming the wave front propagating from 2 to 3 (with a distance of a) within a time interval $\Delta t$, the actual shear wave speed $c_s$ is $a/\Delta t$. If shear wave speed is only measured along the x-direction as was the case in FIG. 1, the apparent shear wave speed $c_{s'}$ will be $b/\Delta t$, which is higher than the real shear wave speed $c_s$. Therefore, when the measurement direction is not aligned with shear wave propagation direction, the estimated shear wave speed will be biased high. This bias effect applies to the in-plane (within the transducer imaging plane) oblique shear waves shown in FIG. 2, as well as out-of-plane (out of the transducer imaging plane) shear waves that travel through the two-dimensional (2D) ultrasound detection plane at an oblique angle.

Here two methods are provided to correct for this bias effect. The first method assumes the medium is homogenous. This can be used to study diffuse diseases where the mechanical properties are expected to change uniformly across the entire organ. Examples include liver fibrosis, lung fibrosis, and changes to the brain in patients with Alzheimer's disease.

k-f Space Method for Homogeneous Media

Consider shear wave motion that can be measured in a 2D spatial plane in the x-z plane as shown in FIGS. 3A and 3B. Referring to FIG. 4, a process for analysis in a homogeneous media begins at process block 100 with acquiring a series of measurements repeatedly through time, t. Then, at process block 102, the data is analyzed. For example, one way to analyze this spatiotemporal data, $u(x,z,t)$, is to apply a Fourier transform along the two spatial dimensions and the temporal dimension to give $U(k_x,k_z,f)$. This frequency domain representation will be referred to as k-f space.

For a given frequency, $f_c$, the directionality of the wave motion can be examined by looking at the distribution of energy of $|U(k_x,k_z,f_c)|$. An in-plane wave propagating at an arbitrary angle will show up as a peak in the k-f space with location $(k_x,k_z,f_c)$. To this end, at process block 104, peaks are identified and used, at process block 106, to determine a direction of wave movement. For example, a peak with a positive $k_x$ coordinate indicates a wave moving to right. A peak with a positive $k_z$ coordinate indicates a wave moving downward. At frequency $f_c$, a ray can be drawn from the origin of the $k_x$-$k_z$ plane to the center of the peak, and the angle of that ray, $\theta=\tan^{-1}(k_z/k_x)$, indicates the wave propagation direction for the wave, and the radius of this component $k_r=\sqrt{k_x^2+k_z^2}$ is related to the shear wave speed $c_s$ by $c_s(f_c)=f_c/k_r$. At process block 108, the location of peaks in k-f space are analyzed to determine similar waves, such as those with the same shear wave speed. For example, multiple waves, propagating at different oblique directions will show up as multiple peaks in the k-f space. At a given temporal frequency f, the peaks from multiple in-plane waves will have equal distance from the origin of the $k_x$-$k_z$ plane and lie on a circle with $k_r=f_c/c_s$ because the medium is homogeneous and therefore shear wave speed should be identical for all propagation directions. Accordingly, at process block 110, shear wave propagation in a homogenous medium can be reported without errors attributable to the above-described bias effect.

Referring to FIG. 5, a case is illustrated where three waves, waves 1, 2, and 3, are present. Wave 1 is on the circle 4 $k_r=f_c/c_s$ traveling upwards to the left. Wave 2 is also on the circle $k_r=f_c/c_s$ and has a larger energy and is traveling downward and slightly to the right. Wave 3 is an out-of-plane wave that has a high wave speed because it is located near the center of the $k_x$-$k_z$ plane. Therefore, the speed of in-plane shear waves propagating at oblique angles can be correctly measured using 2D spatial data.

However, waves that are propagating obliquely to the plane of the measured motion (out-of-plane waves) are subject to a bias effect similar to that illustrated in FIG. 2, and will be measured as propagating faster than the true shear wave speed of the medium. In k-f space, these out-of-plane waves are represented as peaks that lie within the circle 4 as $k_r=f_c/c_s$. In a multi-directional wave field, there are multiple in-plane waves and multiple out-of-plane waves. At a given frequency f in the k-f space, this multi-directional wave field will show up as multiple peaks distributed on and within the circle $k_r=f_c/c_s$. Therefore, the circle in the k-f space can be found with the largest radius (lowest wave speed) that sits on the outer edge of these multiple wave peaks, and use the radius of the circle to calculate the correct shear wave speed.

A method for finding the circle is provided below. The wave energy in all directions is integrated in a circle of radius $k_r$ in the k-f space using the relationships:

$$k_x = k_r \cos(\theta); \tag{3}$$

$$k_z = k_r \sin(\theta); \tag{4}$$

$$S(k_r, f_c) = \int_0^{2\pi} \int_0^{k_r} |U(k_r\cos(\theta), k_r\sin(\theta), f_c)| k_r dk_r d\theta. \tag{5}$$

The $S(k_r,f_c)$ function has a sigmoid shape versus $k_r$ and has its steepest slope at the radial position that has the most energy added. This steepest slope point can be found by finding the maximum in $dS(k_r,f_c)/dk_r$ which is referred to as $k_m$. If there are sufficient in plane shear waves propagating at different directions, $dS(k_r,f_c)/dk_r$ would have a peak at the circle where all the in-plane shear waves sit (the lowest wave speed). This closely correlates with the shear wave speed of the medium as given by:

$$c_s(f_c)=f_c/k_m \tag{6}$$

Figure 6:
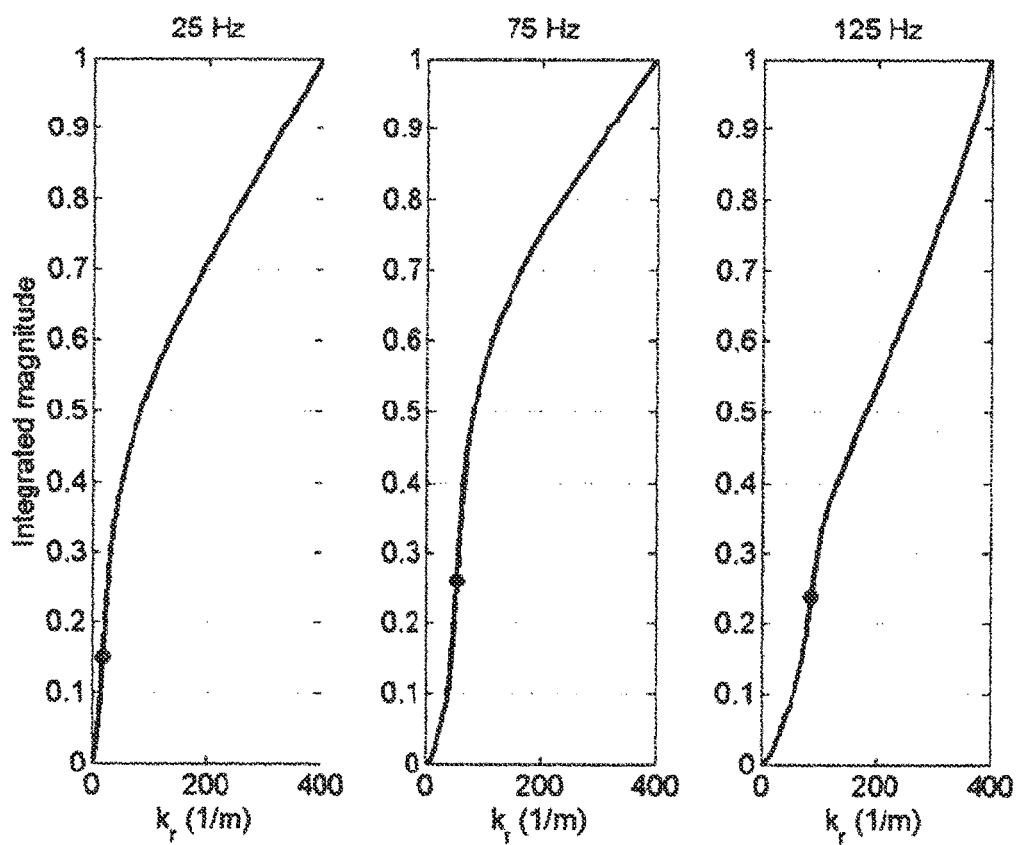
FIG. 6 is a series of graphs showing that integrated results, $S(k_r,f_c)$, from data in FIG. 5 at $f_c$=25, 75, 125 Hz, where the circle depicts the maximum slope of $S(k_r,f_c)$ and the value of $k_m$ used for the phase velocity estimation.
Figure 7:
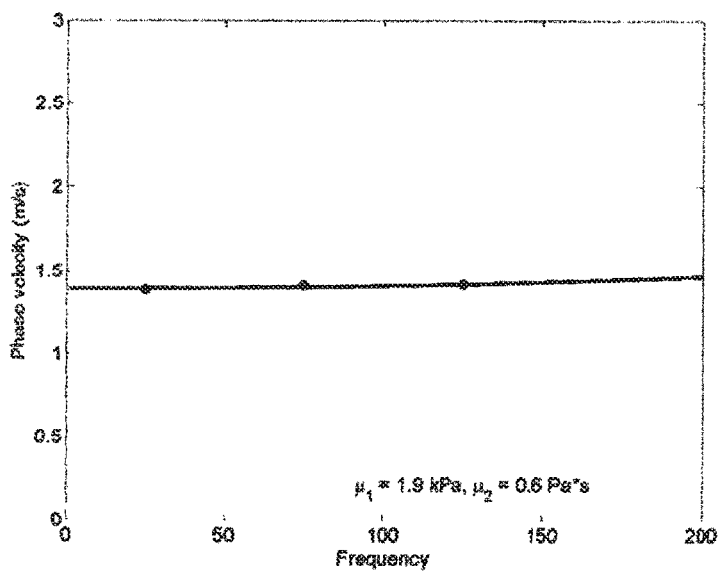
FIG. 7 is a graph of phase velocity dispersion derived using a k-f space method (data point denoted by circles) and fit to Voigt model in Eq. (1) with $\mu_1$=1.9 kPa and $\mu_2$=0.6 Pa·s (solid line).

Experiments were conducted in a homogenous elastic phantom by attaching multiple vibrators to the phantom walls. The vibrators provided an impulsive excitation and were activated in a random fashion to generate shear waves propagating in multiple directions. The process described above was used to evaluate the phase velocities at multiple frequencies, $f_c$. Specifically, the k-f space distributions for the homogeneous phantom for three different shear wave frequencies, $f_c$=25, 75, 125 Hz was studied. To this end, FIG. 6 shows the results from using Eq. (5) on the data acquired. The circles on the graphs depict the location of the maximum slope and the value of $k_m$ used for calculating the phase velocity with Eq. (6). The integrated magnitude continues to increase with $k_r$, even when $k_r$ is larger than $k_m$. This is because the background in FIG. 5 has non-zero values. The phase velocity dispersion for different frequencies is shown in FIG. 7 and the viscoelastic material properties were estimated as $\mu_1$=1.9 kPa and $\mu_2$=0.6 Pa·s by fitting the data to the Voigt model in Eq. (1). These values of $\mu_1$ and $\mu_2$ are close to results obtained by independent validation measurements in this phantom. Although 2D spatial data is used as an example above, the method can be extended to 3D spatial data.

k-f Space Methods for Both Homogeneous and Inhomogeneous Media

Figure 8:
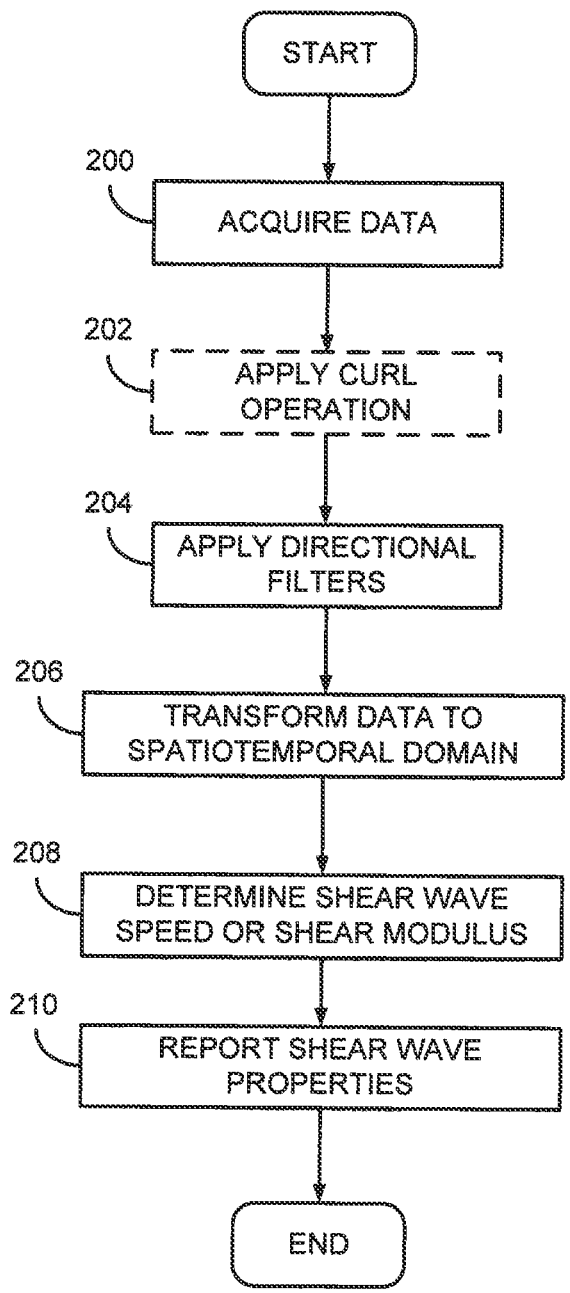
FIG. 8 is a flow chart of a method when analyzing an inhomogeneous medium.

Referring to FIG. 8, for an inhomogeneous medium, a different approach can be used to obtain the spatial distribution of shear wave speed or shear modulus. If the wave motion field is multi-directional, that is, waves are traveling in many different directions, the waves propagating in different directions can be isolated by acquiring data at process block 200. Optionally, at process block 202, a curl operation can be used to remove compressional wave while keeping shear waves. At process block 204, directional filters are applied. The directional filters may be applied in the k-f space by multiplying the directional filter response with the data. An example may include eight directional filters separated by 45 degrees. The following is incorporated herein by reference in its entirety, "Fast shear compounding using directional filtering and two-dimensional shear wave speed calculation, by Song, P., Manduca, A., Zhao, H., Urban, M. W., Greenleaf, J. F., Chen, S., Proceeding of 2013 IEEE International Ultrasonics Symposium, Pages 1264-1267."

To reduce the effects of the out-of-plane shear waves that are measured as waves with a high biased speed, we can additionally filter these out by filtering out the low spatial frequency (k) values for the propagating waves. This can be incorporated into the directional filters by setting a lower limit on the values of $k_l$ for each frequency $f_c$ such that speeds above $c=f_c/k_l$ (i.e., $k_r<k_l$) are eliminated. Similarly, an upper limit of $k_u$ can be set for each frequency $f_c$ such that waves with speed below $c=f_c/k_u$ (i.e., $k_r>k_u$) are eliminated. This lower wave speed limit can be used to remove false "wave motions" caused by body motion or other unwanted interference during shear wave data acquisitions.

For example, the shear wave speed of human liver (from normal to cirrhosis) should be in the range of 1-5 m/s. In this case, the lower and upper limit of shear wave speed can be set to 0.5 and 5 m/s to suppress interfering waves with propagation speed out of this range so that the final shear wave speed estimation is more reliable. For a diffuse disease such as liver fibrosis, the above-disclosed "k-f space method for homogeneous media" can be used to obtain an initial estimate of the shear wave speed of the medium, which can then be used to set the lower and upper shear wave speed limits. For example, in a particular patient, the shear wave speed estimated by "k-f space method for homogeneous media" is 2 m/s. Then the upper speed limit can be set for this particular patient to 3 m/s to improve the rejection of out-of-plane waves and produce a 2D image with less bias. A 2D image will allow the calculation of variation of shear wave speed estimation within the liver as an indication of measurement reliability, and therefore is still valuable even when imaging a homogenous medium. Instead of a lower and higher wave speed limit, fixed thresholds $k_l$ and $k_u$ can be used for all frequencies $f_c$ such that $k_r<k_l$ or $k_r>k_u$ are eliminated.

At very low frequency $f_c$, the resolution of $k_r$ may not be sufficiently small to allow proper elimination of waves based on wave speed limits. One solution is to set a lower temporal frequency limit $f_l$ and eliminate all waves with frequency lower than $f_l$. A smooth ramping profile can be used instead of a unit step function to reduce ringing effects during this process. By way of example, if the shear waves produced by the external vibrations are mainly above 40 Hz, then eliminating all waves with frequency lower than 20 Hz will remove unwanted low frequency motions while keeping the useful shear waves intact. Similarly, an upper temporal frequency limit $f_u$ can be used to remove high frequency noise for more stable results. The speed or frequency limits imposed by hard threshold may create jump discontinuities associated with undesirable Gibbs ringing artifacts. Therefore, a "soft" threshold with smooth transition can be used instead for these limits.

Referring again to FIG. 8, after applying the directional filters at process block 204, an inverse Fourier transform may be applied at process block 206 to bring the data back to the spatiotemporal domain for analysis to, at process block 208, obtain shear wave speed or shear modulus. At process block 210, the properties of the shear wave, including shear wave speed or shear modulus, are reported. As will be described below, this report may include shear wave speed maps and/or information from combine shear wave speed maps from multiple directions.

Figure 9:
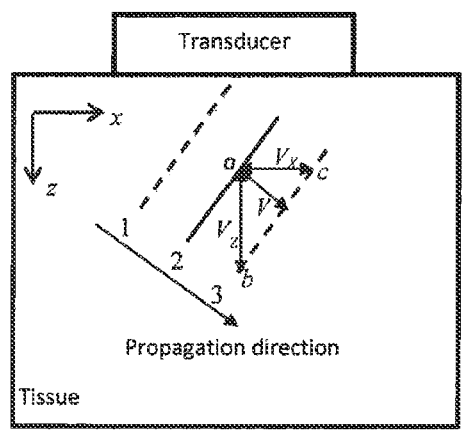
FIG. 9 is a schematic diagram illustrating 2D shear wave speed calculation, where shear wave speeds both along $V_X$ and $V_Z$ directions are calculated to obtain the true shear wave speed V.

For example, the shear wave speed can be estimated using a time-of-flight (TOF) method (for example, M. L. Palmeri, M. H. Wang, J. J. Dahl, K. D. Frinkley, and K. R. Nightingale, "Quantifying hepatic shear modulus in vivo using acoustic radiation force," Ultrasound Med. Biol., vol. 34, pp. 546-558, April 2008., which is incorporated herein by reference in its entirety) or using normalized cross-correlation of the wave motion (for example, M. Tanter, J. Bercoff, A. Athanasiou, T. Deffieux, J. L. Gennisson, G. Montaldo, M. Muller, A. Tardivon, and M. Fink, "Quantitative assessment of breast lesion viscoelasticity: Initial clinical results using supersonic shear imaging," Ultrasound Med. Biol., vol. 34, pp. 1373-1386, September 2008. or J. McLaughlin and D. Renzi, "Using level set based inversion of arrival times to recover shear wave speed in transient elastography and supersonic imaging," Inverse Probl., vol. 22, pp. 707-725, April 2006. or R. S. Anderssen and M. Hegland, "For numerical differentiation, dimensionality can be a blessing" Math. Comput., vol. 68, pp. 1121-1141, 1999, each of which is incorporated herein by reference in its entirety). These are one-dimensional methods, but in the imaging plane we can measure the shear wave speed in two-dimensions (2D), as shown in FIG. 9.

In particular, a normalized cross-correlation can be applied to both x and z directions so that a lateral shear wave speed $V_X$ and an axial shear wave speed $V_Z$ can be obtained. By way of example, let the shear wave signal detected at pixel a, b, and c be $S_a(t)$, $S_b(t)$, and $S_c(t)$, where t is time. Let the time delay estimated by cross-correlation be $t_{ab}$ between $S_a(t)$ and $S_b(t)$, and $t_{ac}$ between $S_a(t)$ and $S_c(t)$. Let distance between pixel a and c be $L_{ac}$, and distance between pixel a and b be $L_{ab}$. Then $V_X=L_{ac}/t_{ac}$, and $V_Z=L_{ab}/t_{ab}$. In the triangle denoted by apex a, b, and c, the true shear wave speed V can be calculated by the formula:

$$V = \frac{V_X V_Z}{\sqrt{V_X^2 + V_Z^2}}, \quad (7);$$

or $$V = \frac{L_{ac} \times L_{ab}}{\sqrt{L_{ac}^2 \times t_{ab}^2 + L_{ab}^2 \times t_{ac}^2}}. \quad (8)$$

Equation (8) is more stable than Eq. (7) when either $t_{ac}$ or $t_{ab}$ is zero (if wave propagation direction is aligned with axis x or z). Note that the 2D vector shear wave speed calculation given by Eqs. (7) and (8) does not require a priori knowledge of the direction of shear wave propagation, which is difficult to know in practice.

Figure 10A:
FIG. 10A is schematic diagram illustrating a conventional local shear wave speed recovery method, where one cross-correlation is calculated between shear wave signals from the left-edge pixel and right-edge pixel of the window.
Figure 10B:
FIG. 10B is a schematic diagram illustrating local shear wave speed estimation method, where multiple cross-correlations are calculated and the final shear wave speed at the center pixel is given by weighted summing these speed estimates by their cross-correlation coefficients.
Figures 11A, 11B:
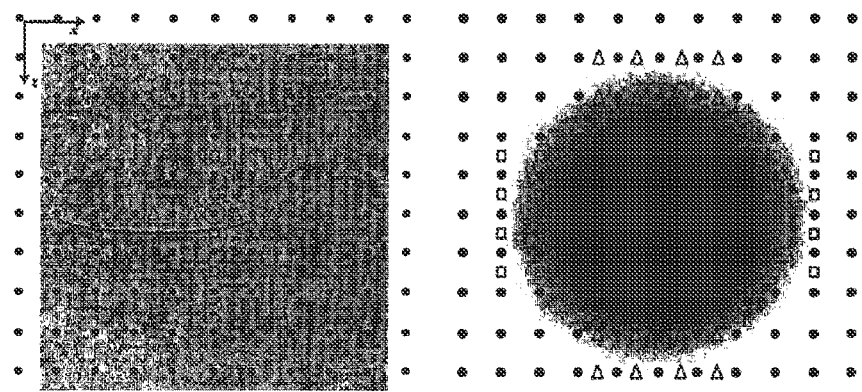
FIG. 11A is a diagram showing a conventional 1D processing window, where the algorithm shown in FIG. 10B was used along both axial and lateral directions to get $V_X$ and $V_Z$, respectively. The dashed curve indicates the pair of pixels used to get the shear wave speed estimate for the upmost square. The solid curve indicates the pair of pixels used to get the shear wave speed estimate for the leftmost triangle. Note that only pixels on lines that cross the center pixel (indicated by the circle) are used.
FIG. 11B is a diagram showing all pixels within the window of FIG. 11A used to get estimates of $V_X$ and $V_Y$. The triangles indicate the spatial locations of estimated $V_X$. The rectangles indicate the spatial locations of estimated $V_Y$. The gradient indicates the distance weighting, where higher weights are assigned to estimates that are closer to the center pixel.

Two methods were developed to increase the robustness of 2D vector shear wave speed calculation while preserving the spatial resolution. First, an algorithm used in numerical differentiation calculation was adapted to local shear wave speed calculation. Conventional local shear wave speed measurement techniques as introduced in M. Tanter, J. Bercoff, A. Athanasiou, T. Deffieux, J. L. Gennisson, G. Montaldo, M. Muller, A. Tardivon, and M. Fink, "Quantitative assessment of breast lesion viscoelasticity: initial clinical results using supersonic shear imaging," Ultrasound Med Biol, vol. 34, pp. 1373-86, September 2008., which is incorporated herein by reference in its entirety, cross-correlate two shear waveforms (waveform of particle displacement or velocity versus time) from two imaging pixels that are a fixed distance apart, as shown in FIG. 10(a), to estimate the shear wave speed of the center pixel. A more robust approach, as shown in FIG. 10(b), cross-correlates multiple pairs of shear waveforms that are a shorter distance apart and produces multiple local shear wave speed estimates. The final shear wave speed at the center pixel is given by weighted summing these estimates by their correlation coefficients. This algorithm can be implemented along both x and z directions to obtain $V_X$ and $V_Z$, as shown in FIG. 11(a). With respect to FIG. 11(b), all pixels within the gray window as in FIG. 11(a) may be used to get estimates of $V_X$ and $V_Z$. The triangles indicate the spatial locations of estimated $V_X$. The rectangles indicate the spatial locations of estimated $V_Z$. The gradient shading indicates the distance weighting: higher weights are assigned to estimates that are closer to the center pixel (indicated by darker gray).

Combine Shear Wave Speed Maps from Multiple Directions

Figure 12:
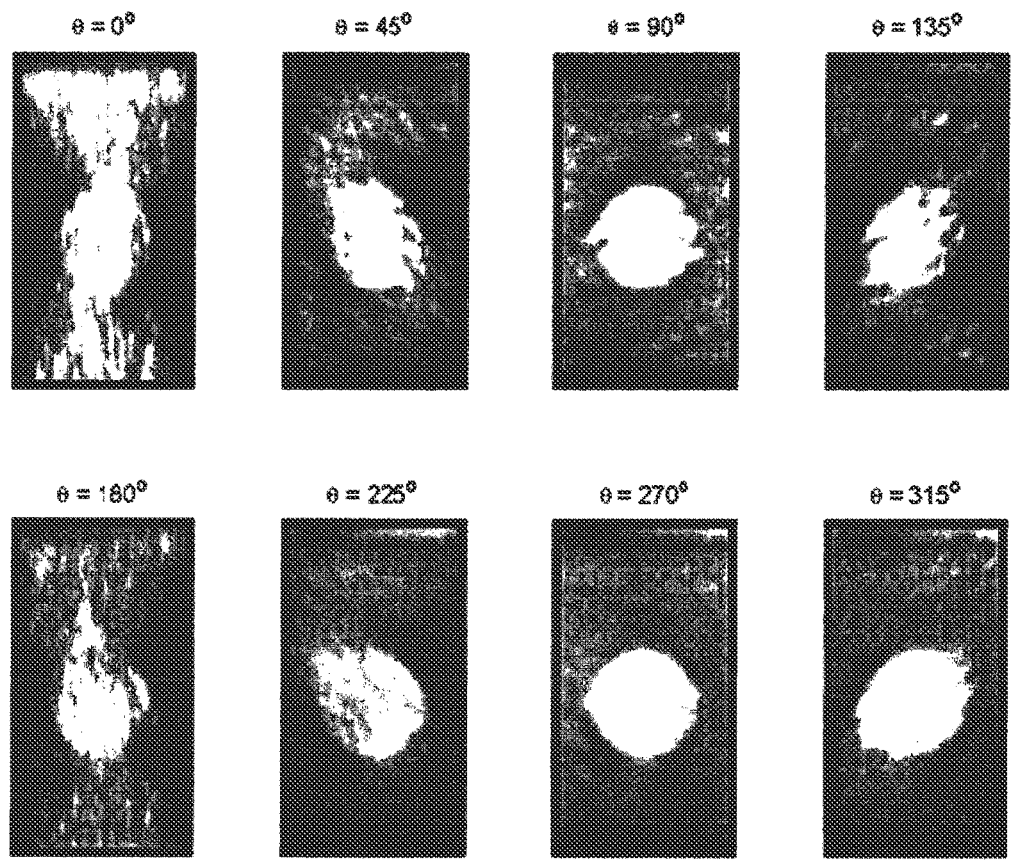
FIG. 12 is a series of images illustrating shear wave speed reconstructions for phantom with inclusion after applying eight directional filters.
Figure 13:
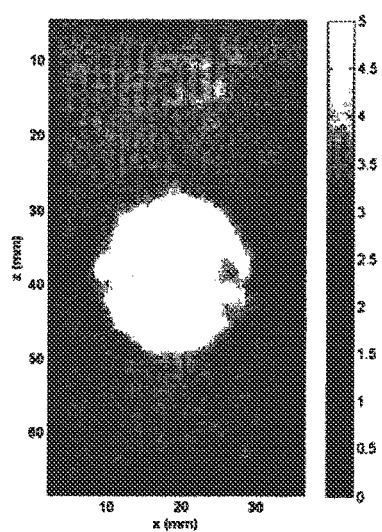
FIG. 13 is an image showing shear wave speed reconstruction after combining the results from eight directional filters, where the scale bar is shear wave speed in m/s.

A total number of D shear wave speed maps are produced from D directional filters with different directions, using the 2D vector calculation method described above. The final shear wave speed map can be obtained from combining the D speed maps. In particular, FIG. 12 shows 8 speed maps (D=8) obtained in a test phantom with a hard inclusion in the middle, after applying the 8 directional filters. Multiple miniature vibrators were attached to the surface of the phantom to produce the complex wave field used in this experiment. FIG. 13 shows the final shear wave speed map obtained by weighted sum of the data in FIG. 12. The weighting used here is the normalized cross-correlation coefficient (NCC) of each pixel in each directional image in FIG. 12. Shear wave energy at each image pixel (the sum of the square of the motion signal over time) in each directional image is also a good quality control factor, and therefore can be used in combination with the NCC to calculate the weighting for each pixel. One can set up thresholds for shear wave energy and NCC so that shear wave speed estimates from pixels with low shear wave energy and poor cross-correlation will not contribute to the final map. Another option of combining multiple directional shear wave images is to take the minimum or median value of all images to produce the final shear wave map. This will suppress the bias caused by out of plane waves and compressional waves, and will work especially well for a homogenous medium.

Figure 14:
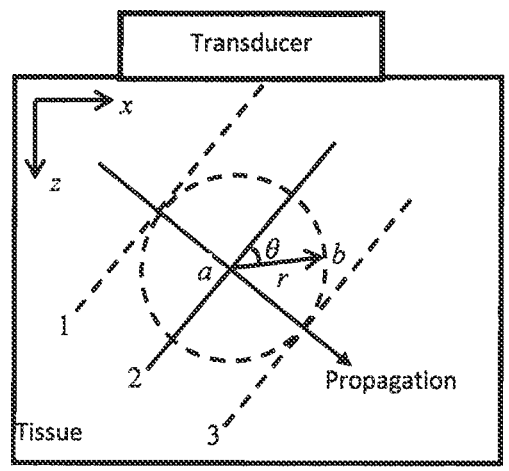
FIG. 14 is a schematic diagram illustrating a delay of a shear wave front measured at an oblique angle to the propagation direction.

After directional filtering, Eqs. (7) and (8) calculate the shear wave speed from two orthogonal directions. Shear wave data in real applications have noise and thus errors in time delay estimation in either x or z direction will enter the final shear wave estimation through Eqs. (7) and (8). In the presence of noise, it is desirable to measure shear wave propagation in multiple directions to improve robustness of final shear wave speed estimation. Referring to FIG. 14, the shear wave front propagates from position 1 to 2 to 3 with a distance interval r. Assuming the time it takes for the shear wave to propagate from 1 to 2 is τ. Propagation from position 2 to 3 will also take time τ. The time delay between the shear wave signal at a (center of circle) and b (on the circle with radius r) is $\tau_{ab} = \tau \cdot \sin(\theta)$, where θ is the angle determined by the location of b as shown in FIG. 14. In reality, the measured delay is $\tau_{ab}(\theta) = \tau \cdot \sin(\theta) + n(\theta)$, where n(θ) is noise. n(θ) at different angles should be independent to each other. Therefore, multiple delays τ(θ) at multiple angles can be measured and fit to a model τ·sin(θ) to obtain a more robust estimate of τ in the presence of noise n(θ). In practical situations, the propagation direction of the shear wave in the x-z coordinate is typically unknown. Therefore, the model used for fitting should be:

$$\tau \cdot \sin(\theta + \phi) \quad (9);$$

where φ is a constant phase offset. Both τ and φ can be determined during the data fitting process. And the shear wave speed is calculated by:

$$V = r/\tau \quad (10).$$

Figure 15:
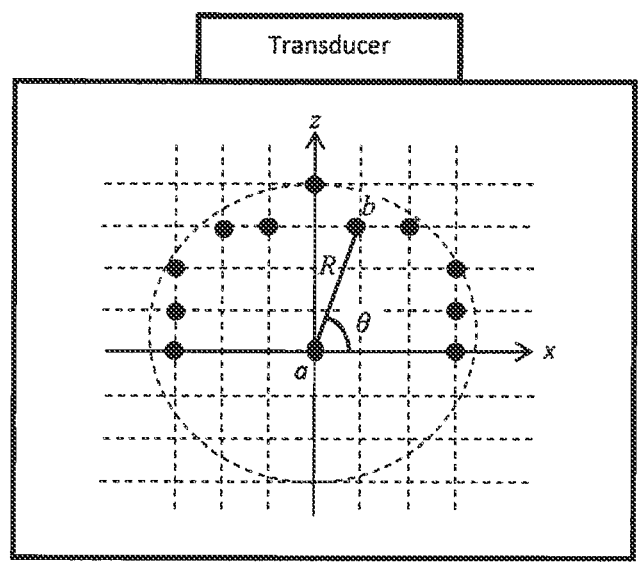
FIG. 15 is a schematic diagram illustrating a scaling of delay measured between two pixels.
Figure 16:
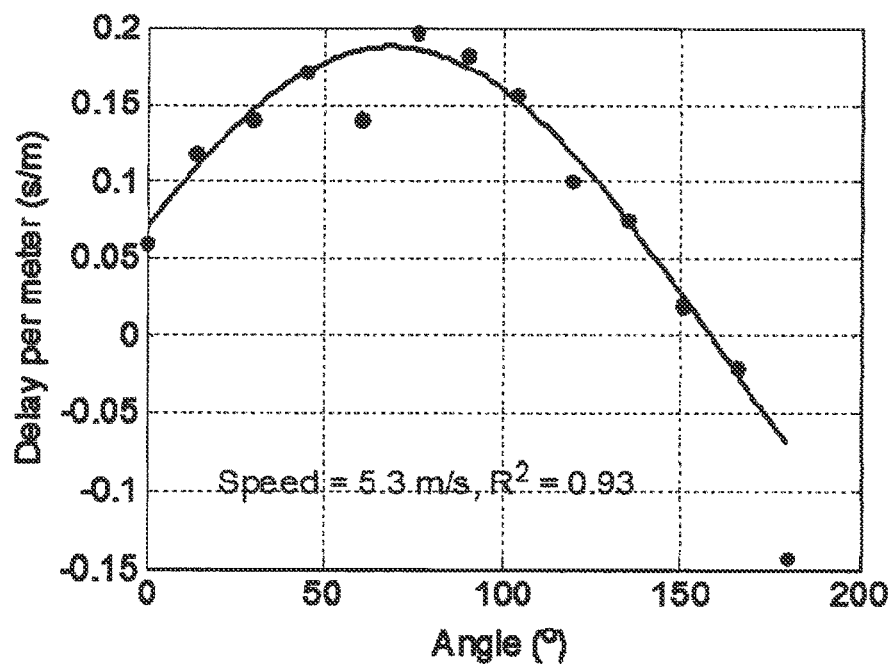
FIG. 16 is a graph showing measurements made in a test phantom with nominal shear wave speed 5.2 m/s. Dots are time delays (normalized by distance) measured at different angles. The solid line is the fitting of the data to a sine model, which gives an amplitude of 0.1884 s/m corresponding to a shear wave speed of 5.3 m/s.

When ultrasound detection of shear wave signal is performed on a Cartesian spatial grid, the delay measured between shear waves detected at 2 pixels needs to be scaled by the distance between these two pixels. Referring to FIG. 15, the black dots denote the pixel location where shear waves are detected. Pixel a locates at the origin, and pixel b locates at (x, z). The distance R between a and b is therefore $R = \sqrt{x^2 + z^2}$, and the angle θ=arctangent(z/x). Assuming the delay measured between pixel a and b is $D_{ab}$, the delay normalized by R is therefore $\tau_{ab} = D_{ab}/R$. Using this approach, $\tau_{ab}(\theta)$ can be measured along multiple angles when other unlabeled black dots in FIG. 11 are selected as pixel b. The measured $\tau_{ab}(\theta)$ is then fit with the model in Eq. (9) to estimate τ, which can be used to calculated the final shear wave velocity with Eq. (10) by setting r=1, because the delays measured here have already been normalized by distance. FIG. 16 shows an example of data obtained in a test phantom with nominal shear wave speed of 5.2 m/s. Dots are time delays (normalized by distance) measured at different angles. The solid line is the fitting of the data to a sine model, which gives an amplitude of 0.1884 s/m corresponding to a shear wave speed of 5.3 m/s. The above model fitting approach uses the delay in multiple directions to calculate the final shear wave speed. Similar to the relationship between Eqs. (7) and (8), apparent wave speeds instead of delays in multiple directions can also be used to calculate the final shear wave speed. The approach shown in FIGS. 10 and 11 can be combined with the model fitting approach to make the method more robust. In addition, each pixel will have a $R^2$ value indicating the quality of the model fitting with delay through Eq. (9) or with speed. Therefore, the $R^2$ value can be used to control the weighting of the shear wave speed maps for different directions to produce a final shear wave speed map.

Other than time-of-flight method and normalized cross-correlation method, phase lag method ("Shear wave spectroscopy for in vivo quantification of human soft tissues visco-elasticity" IEEE Trans. Med. Imaging, vol. 28, pp. 313-322, 2009) can also be used to estimate frequency dependent wave propagation speed (phase speed) using spatiotemporal data after directional filtering. In the phase lag method, a Fourier transform, Kalman filtering, or other appropriate methods are performed on the time signal at each pixel to calculate the phase of the shear wave at multiple frequencies. The shear wave speed at a given frequency f is then estimated from phase lag at frequency f of at least two pixels along the shear wave propagation direction. The phase lag method can resolve wave propagation speed at multiple frequencies (dispersion), and can be extended to calculate phase speed for waves propagating from unknown directions using Eq. (7). When time delays in Eqs. (8) through (10) are used instead, the time delay t can be computed from the phase lag p and the frequency f of the shear wave:

$$t = \frac{p}{2\pi f}.$$

Although 2D spatial data is used as an example above, the method can be extended to 3D spatial data.

The above disclosed method needs all pixels of the spatiotemporal data to have the same time grid. This requirement can be met when "flash imaging" is used for pulse echo detection of shear waves. For traditional ultrasound scanners where the 2D data are acquired in a line-by-line or zone-by-zone manner, pixels at different ultrasound A-lines are sampled at different time grid. In such situation, the time signal at each pixel can be interpolated to a higher sampling rate such that the post-interpolation time samples are aligned on the same time grid for different pixels. One example of a system and method for interpolation and alignment is described in co-pending U.S. Provisional Application Ser. No. 61/710,744, filed on Oct. 7, 2012, and PCT Application No. US2013/063631, filed Oct. 7, 2013, both of which are incorporated herein by reference in their entirety.

Figure 17A:
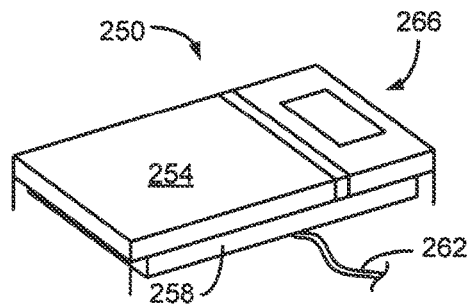
FIGS. 17A and 17B are perspective views of systems for delivering vibrations to a subject in accordance with the present invention.
Figure 17B:
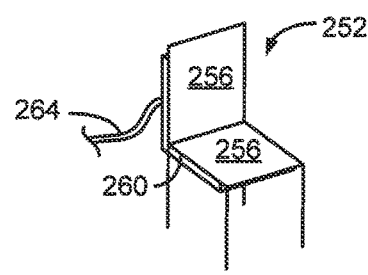

Systems and methods of efficiently producing shear waves from external vibration are also disclosed here. For example, referring to FIGS. 17A and 17B, a piece of furniture, such as a bed 250 or a chair 252 or other structure having a rigid surface or surfaces 254, 256 can be used to vibrate the subject or medium (not shown) engaged with the rigid surface 254, 256. The rigid surface 254, 256 can be flat or curved to optimize vibration transmission into the body. A vibration source 258, 260 is coupled to the rigid surface 254, 256. As will be described, the vibration source 258, 260 may include a motor with off-center weight or other appropriate sources of vibrations, such as pneumatic or acoustically delivered vibrations, that delivers vibrations to a subject or medium through the rigid surface 254, 256. In this regard, the vibration source may include a connection 262, 264 that connects to a driving or power source. To this end, as will be described, depending upon the design of the vibration source 258, 260 the connection 262, 264 may be an electrical connection or may be a pneumatic or acoustic connection or other means of receiving driving energy to operate the vibration source 258, 260

Cushions 266 can be added between the rigid surface 254, 256 and the body to improve patient comfort. In addition to traditional cushion materials such as foams and rubbers, liquid or air sealed inside a flexible membrane can also serve as a deformable cushion that can conform to the body surface to maximize contact area for more efficient vibration delivery. Because the air or liquid is sealed in a closed space, vibration from the rigid surface can transmit through the air or liquid cushion efficiently into the body. The air or liquid cushion can be integrated with the rigid surface 254, 256.

It is contemplated that the vibration source 258, 260 may include a large vibration source in some designs, such as a motor carrying an offset load. In other configurations, instead of one large source of vibrations, multiple vibration sources may be positioned at different locations along the rigid surface 254, 256 to produce shear waves in the body. Alternatively, vibration sources can be secured directly to a body surface of the subject or medium, such as by elastic strap, adhesive membrane, or other appropriate means. Further still, the vibration sources can be embedded in cushions 266 for the patient to lie on, or embedded in a vest or other clothing for the patient to wear.

As mentioned DC motors with off-centered weight is one example of a system that may be used. In some cases, the DC motors may be as small as those used cell phone vibrators. Alternatively, larger electromagnetic actuators can be used to produce stronger shear waves in deeper regions from the body surface. Also, a pneumatic or other driver used by Magnetic Resonance Elastography (MRE) can be used for this purpose. Examples of such MRE driver systems may be found in U.S. Pat. Nos. 6,037,774; 7,034,534; 7,307,423; 8,508,229; and 8,615,285 and Application Nos. 2012/0259201 and 2012/0271150, each of which are incorporated herein by reference in their entirety. When ultrasound is used for shear wave detection, electromagnetic interference is not of concern. Thus, electromagnetic devices can be used as vibration sources.

Figure 17C:
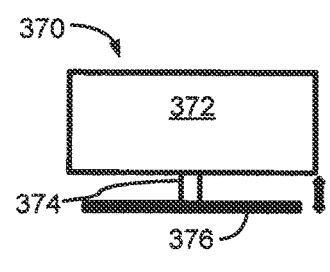
FIG. 17C is a schematic illustration of electromagnetic actuators, where "push" action where the contact plate and the actuator body move away from each other upon activation.
Figure 17D:
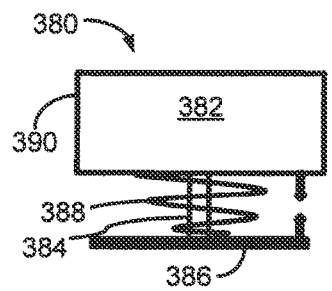
FIG. 17D is a schematic illustration of electromagnetic actuators, where "pull" action where the contact plate and the actuator body move towards each other upon activation.

Regardless of the specific means of generating or driving the vibrations, there are some basic configurations that can be used to select generation or driving sources for the vibration sources. For example, as shown in FIG. 17C, one type of actuator 370 has a "push" motion when activated. Such actuators 370 can be pressed against the body surface, for example, using elastic straps or other appropriate means. Upon activation, an actuation body 372 pushes, by way of a shaft 374, on a contact plate 376 to produce a small "punch" to the body surface to generate shear waves inside the body. In another configuration, referring to FIG. 17d, an actuator 380 may utilize a "pull" motion when activated. In this configuration, the actuator is inside the actuation body 382 is connected through a shaft 384 to the contact plate 386. However, a spring or other appropriate biasing mechanism 388 may be inserted between the actuator body 382 and the contact plate 386 to maintain separation of these two parts. The contact plate 386 is fixed to a case 390 of the actuation body 382 and the actuator is free to move and slide along the shaft 384. Upon activation, the actuator body 382 accelerates and moves towards the contact plate 386. The inertial mass of the actuator body 382 will produce an impact to the patient body for shear wave generation when it strikes the contact plate 386. When the actuator is not activated, the bias mechanism 388 will separate the actuator body 382 and the contact plate 386 to provide an adequate distance for acceleration of the actuator body 382 for the next impact.

As discussed, multiple sources of vibration may be used. When multiple sources of vibrations are used to produce shear waves in a patient study, electric current drawn from a common source driving these vibrators can be very high, requiring a high power source. To solve this issue, a control circuit may be used to connect the driving source and the multiple vibrators. The control circuit connects the source with each of the multiple vibrators only for a brief period of time. The "ON" time of each vibrator can be purposely misaligned such that at any given time instant, the source is only powering one or a few vibrators. By way of example, assume one source is driving 10 vibrators. Each vibrator is turned on for 10 milliseconds (ms) to produce shear waves in the patient body. The control circuit can sequentially turn on and off each vibrator such that vibrator 1 is turned ON during 0-10 ms, vibrator 2 is turned ON during 10-20 ms, vibrator 3 is turned ON during 20-30 ms, . . . , vibrator 10 is turned ON during 90-100 ms. In this manner, the source only needs to drive one vibrator at a time, thus reducing the current and power requirement of the source.

An air or underwater loudspeaker can also be used to introduce vibration in body. The frequency of sound emitted by the loudspeaker can be adjusted to the resonant frequency of the body part where vibrations are to be introduced. For example, resonance may help introducing vibration in liver for shear wave elasticity measurements. In this case, the loudspeaker can be embedded within an examination bed with the active surface facing up and roughly level with the bed surface. The patient can lie on the bed facing upwards with the upper back positioned on top of the loud speaker. The opening of the bed for embedding the loud speaker should be large enough to allow sufficient transmission of acoustic energy from the loud speaker into the body. The opening should also not be too large so that it is completely covered and preferably sealed by the patient's back when the patient lies on the bed. Frequency of the sound emitted by the load speaker can be adjusted to match the resonant frequency of the chest cavity of the patient, for example at 50 Hz. Alternatively, a chirp signal (for example, from 30 to 80 Hz) can be emitted into the body for shear wave production. Then vibration from the rib cage and lung will propagate with the body to produce multi-directional shear waves in liver.

The methods disclosed here assume a plane wave propagating in a homogenous medium. In practice, this assumption can be considered valid locally. For example, within a 5 mm by 5 mm area, the shear wave can be considered as plane wave and the medium can be considered homogeneous.

Although shear waves is used as an example in this teaching, the methods disclosed here can be used to measure speed of other waves such as compressional waves. And shear waves can be detected by methods other than ultrasound, such as magnetic resonance imaging (MRI) or optical systems. For all detection methods, wave motion component (usually a 3D vector) in the x direction, y direction, z direction, or their combination when available, can be used with the above method for shear wave speed measurements.

Figure 18:
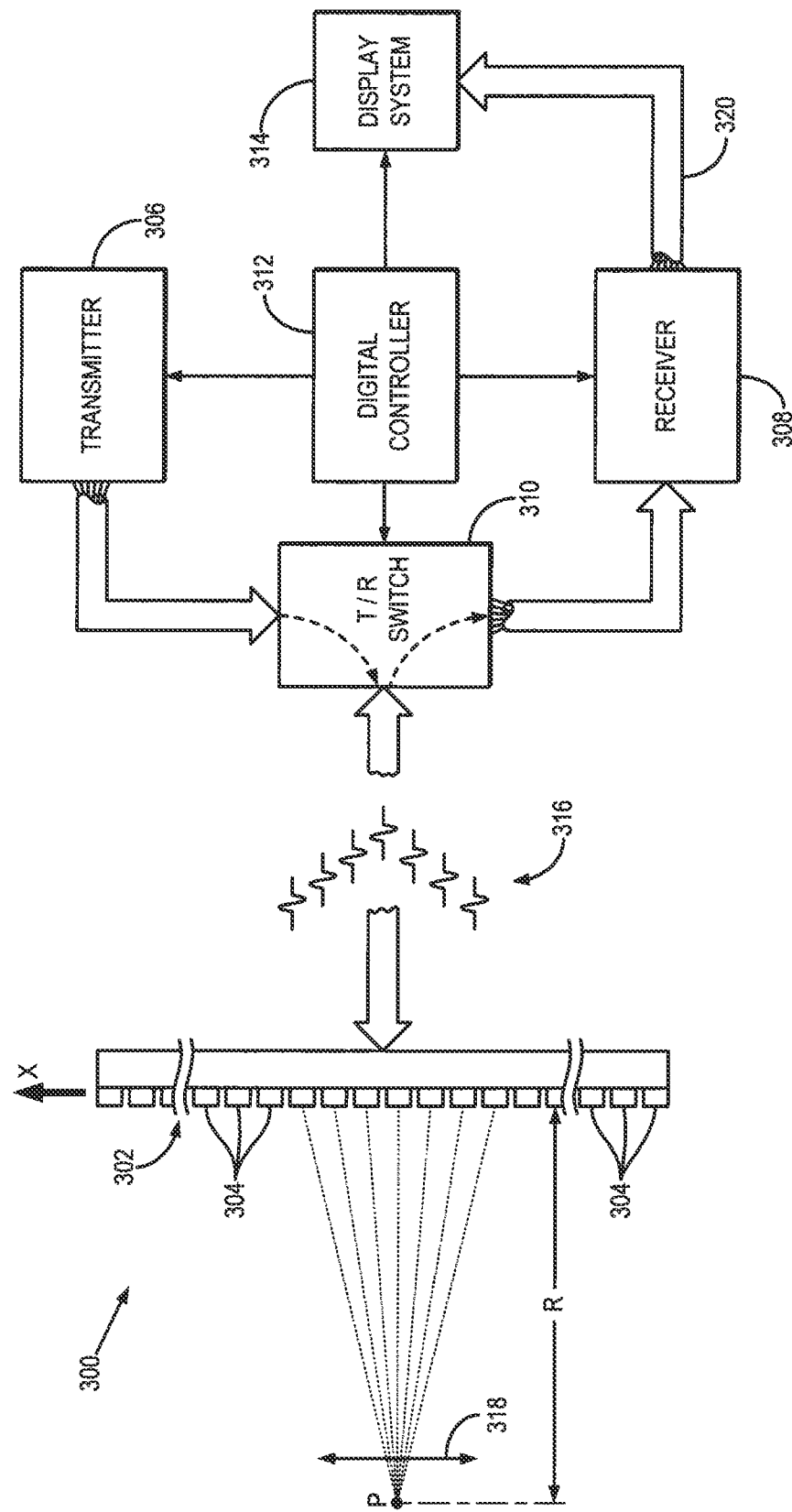
FIG. 18 is a block diagram of an example ultrasound system configured for use with implementing the present invention.

Referring now to FIG. 18, an example of an ultrasound imaging system 300 that may be used with the present invention is illustrated. It will be appreciated, however, that other suitable ultrasound systems can also be used to implement the present invention. The ultrasound imaging system 300 includes a transducer array 302 that includes a plurality of separately driven transducer elements 304. When energized by a transmitter 306, each transducer element 302 produces a burst of ultrasonic energy. The ultrasonic energy reflected back to the transducer array 302 from the object or subject under study is converted to an electrical signal by each transducer element 304 and applied separately to a receiver 308 through a set of switches 310. The transmitter 306, receiver 308, and switches 310 are operated under the control of a digital controller 312 responsive to the commands input by a human operator. A complete scan is performed by acquiring a series of echo signals in which the switches 310 are set to their transmit position, thereby directing the transmitter 306 to be turned on momentarily to energize each transducer element 304. The switches 310 are then set to their receive position and the subsequent echo signals produced by each transducer element 304 are measured and applied to the receiver 308. The separate echo signals from each transducer element 304 are combined in the receiver 308 to produce a single echo signal that is employed to produce a line in an image, for example, on a display system 314.

The transmitter 306 drives the transducer array 302 such that an ultrasonic beam is produced, and which is directed substantially perpendicular to the front surface of the transducer array 302. To focus this ultrasonic beam at a range, R, from the transducer array 302, a subgroup of the transducer elements 304 are energized to produce the ultrasonic beam and the pulsing of the inner transducer elements 304 in this subgroup are delayed relative to the outer transducer elements 304, as shown at 316. An ultrasonic beam focused at a point, P, results from the interference of the separate wavelets produced by the subgroup of transducer elements 304. The time delays determine the depth of focus, or range, R, which is typically changed during a scan when a two-dimensional image is to be performed. The same time delay pattern is used when receiving the echo signals, resulting in dynamic focusing of the echo signals received by the subgroup of transducer elements 304. In this manner, a single scan line in the image is formed.

To generate the next scan line, the subgroup of transducer elements 304 to be energized are shifted one transducer element 304 position along the length of the transducer array 302 and another scan line is acquired. As indicated at 318, the focal point, P, of the ultrasonic beam is thereby shifted along the length of the transducer 302 by repeatedly shifting the location of the energized subgroup of transducer elements 304.

Figure 19:
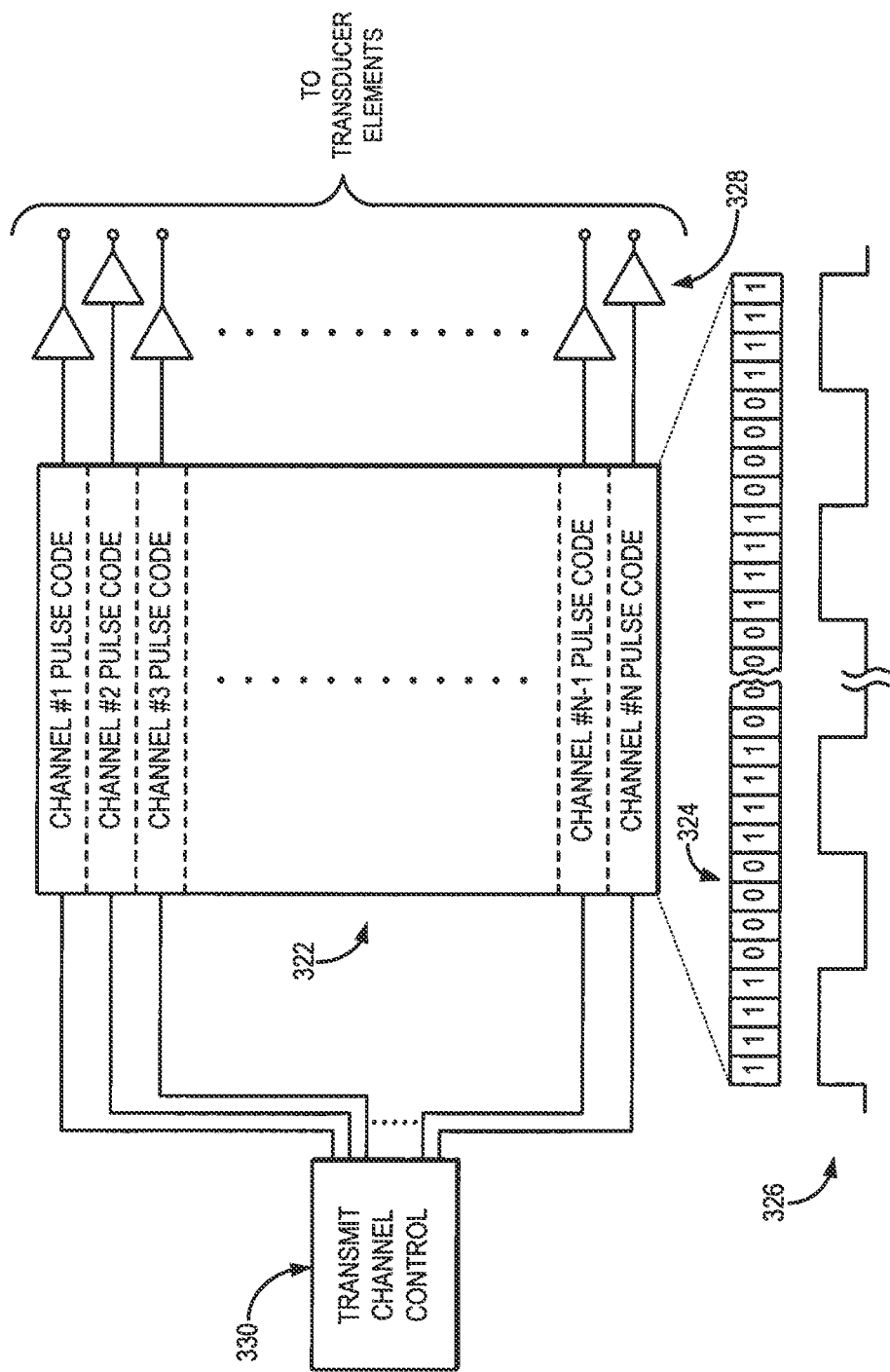
FIG. 19 is a block diagram of an example of a transmitter that forms a part of the ultrasound system of FIG. 18.

Referring particularly to FIG. 19, the transmitter 306 includes a set of channel pulse code memories, which are indicated collectively at 322. In general, the number of pulse code memories 322 is equal to the number of transducer elements 304 in the transducer 302. These pulse code memories are also referred to as transmission channels for this reason. Each pulse code memory 322 is typically a 1×N bit memory that stores a bit pattern 324 that determines the frequency of the ultrasonic pulse 326 that is to be produced. This bit pattern 324 may be read out of each pulse code memory 322 by a master clock and applied to a driver 328 that amplifies the signal to a power level suitable for driving the transducer 302. In the example shown in FIG. 4, the bit pattern is a sequence of four "1" bits alternated with four "0" bits to produce a five megahertz ultrasonic pulse 326. The transducer elements 304 to which these ultrasonic pulses 326 are applied respond by producing ultrasonic energy. If all of the available bits are used, a pulse with a narrow bandwidth centered on the carrier frequency will be emitted.

Figure 20:
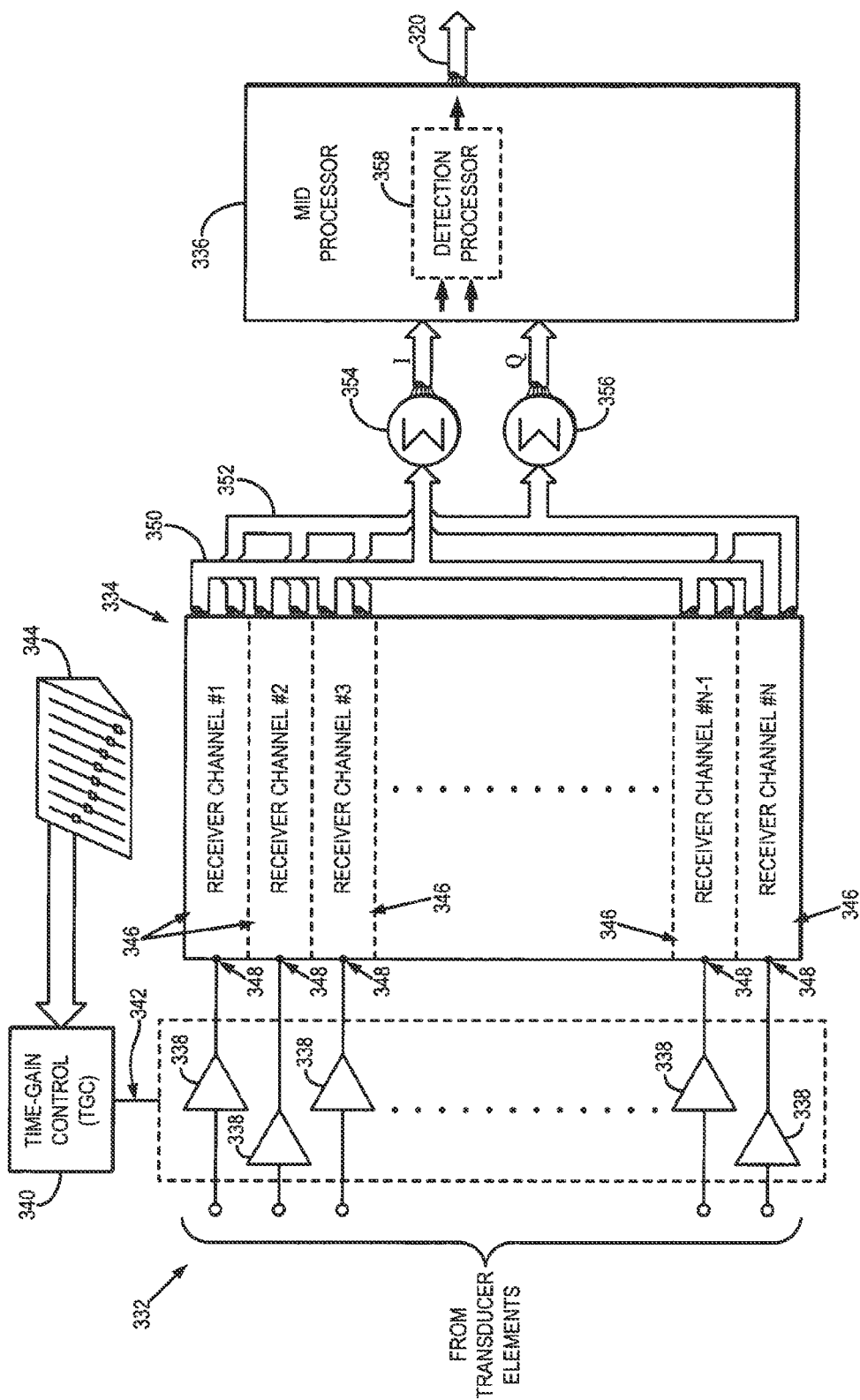
FIG. 20 is a block diagram of an example of a receiver that forms a part of the ultrasound system of FIG. 18.

Referring particularly to FIG. 20, the receiver 308 is comprised of three sections: a time-gain control section 332, a beam forming section 334, and a mid-processor section 336. The time-gain control section 332 includes an amplifier 338 for each receiver channel in the receiver 308, and a time-gain control circuit 340. The input of each amplifier 338 is connected to a respective one of the transducer elements 304 to receive and amplify the echo signal that is receives from the respective transducer element 304. The amount of amplification provided by the amplifiers 338 is controlled through a control line 342 that is driven by the time-gain control circuit 340. As the depth, or range, R, of the echo signal increases, its amplitude is diminished. As a result, unless the echo signal emanating from more distant reflectors is amplified more than the echo signal from nearby reflectors, the brightness of the image diminishes rapidly as a function of range, R. This amplification is controlled by a user who manually sets time-gain control potentiometers 344 to values that provide a relatively uniform brightness over the entire range of the sector scan. The time interval over which the echo signal is acquired determines the range from which it emanates, and this time interval is divided into, for example, eight segments by the time-gain control circuit 340. The settings of the time-gain control potentiometers 344 are employed to set the gain of the amplifiers 338 during each of the respective time intervals so that the received echo signal is amplified in ever increasing amounts over the acquisition time interval.

The beam forming section 334 of the receiver 308 includes a plurality of separate receiver channels 346. As will be explained in more detail below, each receiver channel 346 receives an analog echo signal from one of the amplifiers 338 at an input 348, and produces a stream of digitized output values on an in-phase, I, bus 350 and a quadrature, Q, bus 352. Each of these I and Q values represents a sample of the echo signal envelope at a specific range, R. These samples have been delayed in the manner described above such that when they are summed with the I and Q samples from each of the other receiver channels 346 at summing points 354 and 356, they indicate the magnitude and phase of the echo signal reflected from a point, P, located at range, R, on the steered beam, θ.

The mid-processor section 336 receives beam samples from the summing points 354 and 356. The I and Q values of each beam sample may be, for example, a 16-bit digital number that represents the in-phase, I, and quadrature, Q, components of the magnitude of the echo signal from a point (R, θ) The mid-processor 336 can perform a variety of calculations on these beam samples, the choice of which is determined by the type of imaging application at task.

The present invention has been described in terms of one or more preferred embodiments, and it should be appreciated that many equivalents, alternatives, variations, and modifications, aside from those expressly stated, are possible and within the scope of the invention.

What is claimed is:

1. A method of measuring material properties of a medium, comprising steps of:
   a) producing a multi-directional wave field in the medium;
   b) detecting, with a detection system capable of detecting wave fields propagating in the medium, the multi-directional wave field in at least two spatial dimensions over at least one time instance;
   c) determining a lowest wave propagation speed from the detecting of step b);
   d) calculating at least one of wave speed and material properties of the medium based on the determining of step c); and
   e) generating a report indicating the at least one of wave speed and material properties of the medium.

2. The method of claim 1, wherein the material properties are mechanical properties including at least one of frequency dependent wave speed, storage modulus, and loss modulus.

3. The method of claim 1, wherein step a) includes applying at least one of external vibrations, physiological motions, and ultrasound radiation force to the medium to produce the multi-directional wave field as a mechanical wave field.

4. The method of claim 1, wherein step b) includes controlling at least one of an ultrasound system, an optical system, and magnetic resonance imaging (MRI) system to perform the detecting of the wave field.

5. The method of claim 1, wherein step c) includes calculating a shear wave speed.

6. The method of claim 5, wherein calculating the shear wave speed includes determining a frequency dependence.

7. The method of claim 1, wherein step c) includes determining a lowest shear wave speed at a selected temporal frequency, $f_c$, using a wave component in a Fourier-transformed k-f space at $f_c$ with a largest distance from the origin of k-f space.

8. The method of claim 7, wherein the lowest shear wave speed is calculated at a presence of multi-direction shear waves and compressional waves, by:
   i) integrating at least one of wave energy and amplitude in k-f space within a circle of changing radius centered at the k-f space origin;
   ii) finding a largest radius, $k_m$, where the integrating of step i) increases most rapidly with k; and
   iii) calculating the lowest shear wave speed at temporal frequency $f_c$ by $c_s(f_c)=f_c/k_m$.

9. The method of claim 1, wherein step b) includes performing at least one of line-by-line and zone-by-zone sequential detection of the wave field using ultrasound data that is interpolated and aligned in a time grid.

10. A method of producing images of properties of an object, comprising steps of:
    a) producing a multi-directional wave field in the object;
    b) using an imaging device, acquiring data about the multi-directional wave field in at least two spatial dimensions over at least one time instance;
    c) separating the data acquired in step b) into component data propagating in different directions;
    d) calculating at least two wave components pointing at different spatial directions from the component data;
    e) producing a wave speed map for each propagation direction using the wave components; and
    f) combining the wave speed maps to produce at least one of a speed image and material property image for the object.

11. The method of claim 10, wherein the at least one of the speed image and the material property image indicate at least one of wave speed, storage modulus, and loss modulus.

12. The method of claim 11, wherein step a) includes producing the multi-directional wave field using at least one of external vibrations, physiological motions, and ultrasound radiation force.

13. The method of claim 10, wherein the imaging device includes one of an ultrasound system, optical system, and a magnetic resonance imaging (MRI) system.

14. The method of claim 10, wherein step c) includes using a directional filter in a Fourier transformed k-f domain to separate the data.

15. The method of claim 10, wherein the wave speed map is a map of shear wave speed.

16. The method of claim 10, wherein step d) includes calculating the wave components by cross-correlation.

17. The method of claim 16, wherein the component data includes image data having pixels and the cross-correlation uses multiple pairs of pixels in the image data cross correlated to calculate a wave speed of a center pixel by weighting at least one of a normalized cross-correlation coefficient and a distance of a pair of pixels to the center pixel.

18. The method of claim 10, wherein step f) includes creating a weighted sum of the wave speed maps for different directions.

19. The method of claim 10, wherein step f) includes determining one of a minimum and median value of the wave speed maps for different directions.

20. The method of claim 10, wherein the wave components in step d) include one of delay measured over known distance, measured delay divided by known distance, and known distance divided by measured delay.

21. The method of claim 10, wherein step d) includes calculating the at least two wave components in orthogonal spatial directions.

22. The method of claim 10, wherein step e) includes calculating the wave speed map by fitting the wave components to a model.

23. The method of claim 10, wherein step d) includes imposing at least one of wave speed limits, spatial frequency limits, and temporal frequency limits.

24. The method of claim 10, wherein step b) includes performing at least one of line-by-line and zone-by-zone sequential detection of the wave field using ultrasound and interpolating and aligning a wave field data in a time grid.

25. The method of claim 10, wherein a wave field step is produced by generating vibrations thorough at least one of vibrators, loudspeakers, a vibrating bed, and a vibrating chair.

26. The method of claim 10, where a wave field step is produced using vibrators making impact with mass inertia.

27. A system for measuring material properties of a medium comprising:
a vibration source configured to produce a multi-directional wave field in the medium;
a detector configured to acquire data about the multi-directional wave field in at least two spatial dimensions over a period of time;
a processor configured to:
receive the data from the detection system;
determine a lowest wave propagation speed from the data;
calculate at least one of wave speed and material properties of the medium based on the lowest wave speed; and
generate a report indicating the at least one of wave speed and material properties of the medium.

28. The system of claim 27 wherein the vibration source includes at least one of vibration driver, a loudspeaker, a vibrating bed, and a vibrating chair.

29. A system of producing images of properties of an object comprising:
a vibration source configured to produce a multi-directional wave field in a medium;
a detector configured to acquire data about the multi-directional wave field in at least two spatial dimensions over at least one time instance;
a processor configured to:
a) produce the multi-directional wave field in the object via the vibration source;
b) use an imaging device, to acquire data about the multi-directional wave field in at least two spatial dimensions over at least one time instance;
c) separate the data acquired in step b) into component data propagating in different directions;
d) calculate at least two wave components pointing at different spatial directions from the component data;
e) produce a wave speed map for each propagation direction using the wave components; and
f) combine the wave speed maps to produce at least one of a speed image and material property image for the object.

* * * * *

UNITED STATES PATENT AND TRADEMARK OFFICE
CERTIFICATE OF CORRECTION

PATENT NO.       : 9,622,711 B2
APPLICATION NO.  : 14/398854
DATED            : April 18, 2017
INVENTOR(S)      : Heng Zhao et al.

Page 1 of 1

It is certified that error appears in the above-identified patent and that said Letters Patent is hereby corrected as shown below:

In the Specification

Column 5, Line 24, "of a)" should be --of $\alpha$)--.

Column 5, Line 25, "is a/$\Delta$t" should be --is $\alpha/\Delta t$--.

Signed and Sealed this
Fourteenth Day of November, 2017

Joseph Matal
*Performing the Functions and Duties of the
Under Secretary of Commerce for Intellectual Property and
Director of the United States Patent and Trademark Office*